United States Patent [19]

Wallace

[11] 4,178,103

[45] Dec. 11, 1979

[54] LIGHT SCATTERING PHOTOMETER AND SAMPLE HANDLING SYSTEM THEREFOR

[75] Inventor: Richard W. Wallace, Los Altos, Calif.

[73] Assignee: Chromatix, Inc., Mountain View, Calif.

[21] Appl. No.: 781,740

[22] Filed: Mar. 28, 1977

[51] Int. Cl.² ............................................ G01N 15/02
[52] U.S. Cl. .................................. 356/336; 356/338; 356/246
[58] Field of Search ............... 356/102, 103, 246, 208; 250/574

[56] References Cited

U.S. PATENT DOCUMENTS

| | | | |
|---|---|---|---|
| 2,535,181 | 12/1950 | Way | 356/208 X |
| 3,669,542 | 6/1972 | Capellaro | 356/102 X |
| 3,691,391 | 9/1972 | Kishi | 356/208 X |
| 3,758,787 | 9/1973 | Sigrist | 356/208 X |
| 3,786,261 | 1/1974 | Tucker | 356/102 X |
| 3,843,268 | 10/1974 | Kaye | 356/246 |
| 3,850,525 | 11/1974 | Kaye | 356/103 X |
| 4,027,973 | 6/1977 | Kaye | 356/103 X |

*Primary Examiner*—John K. Corbin
*Assistant Examiner*—Matthew W. Koren
*Attorney, Agent, or Firm*—Flehr, Hohbach, Test, Albritton & Herbert

[57] ABSTRACT

A laser photometer including means forming an unsupported curtain of liquid sample, means for focusing a laser beam at a sample volume in the unsupported liquid curtain, means for receiving a cone of light issuing from the sample in an incremental angle $\Delta\theta$ at an angle $\theta$, means for focusing the cone of light at a field stop and a detector for receiving the power passing through the aperture.

10 Claims, 5 Drawing Figures

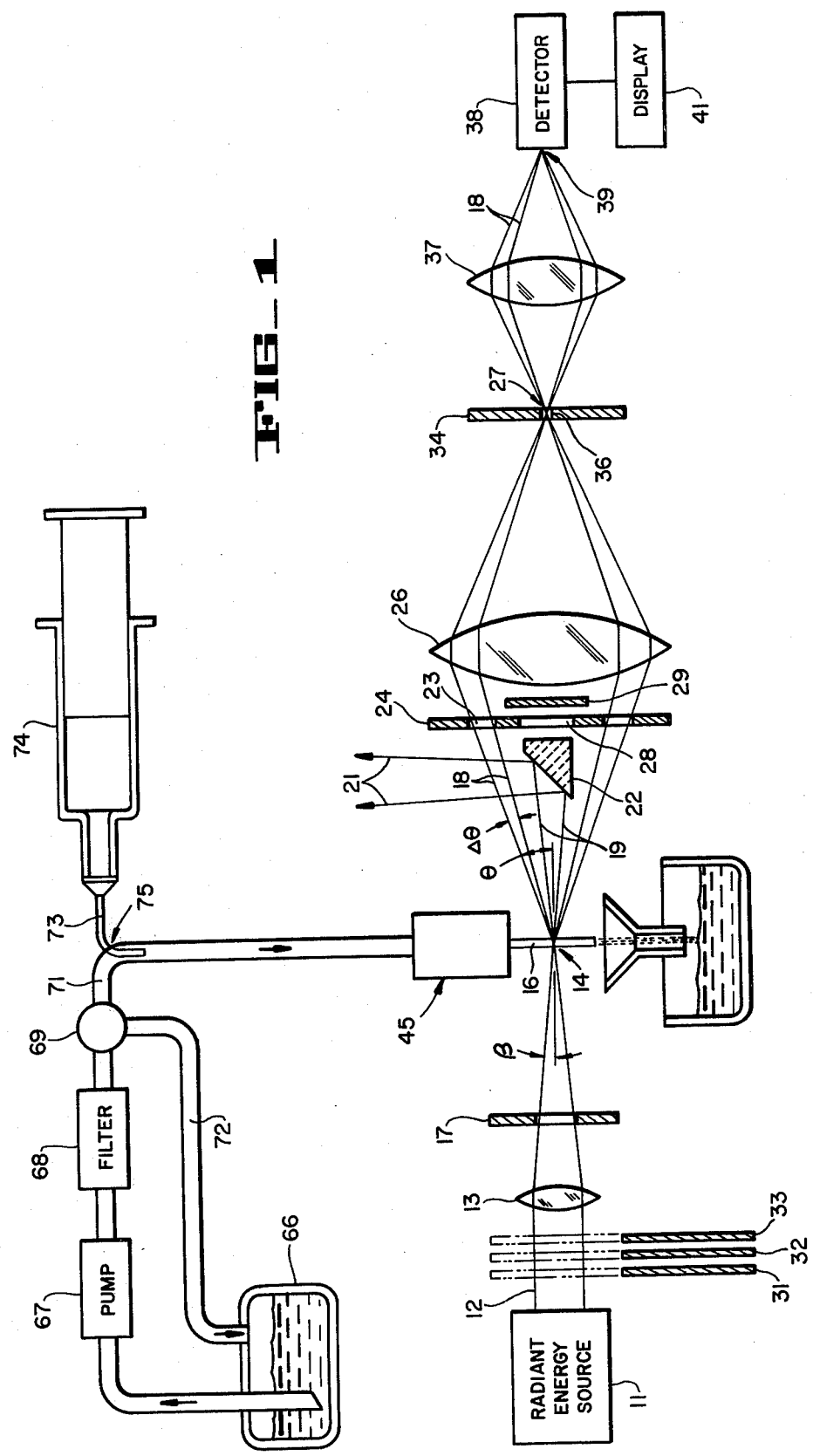
FIG_1

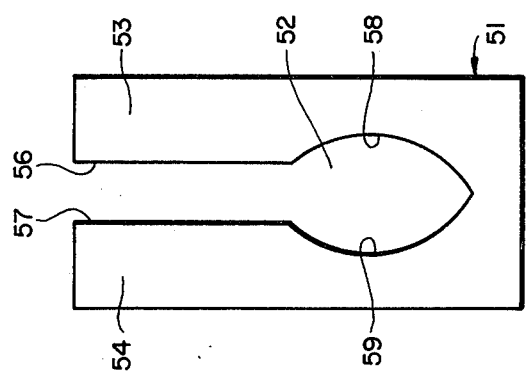
FIG_5
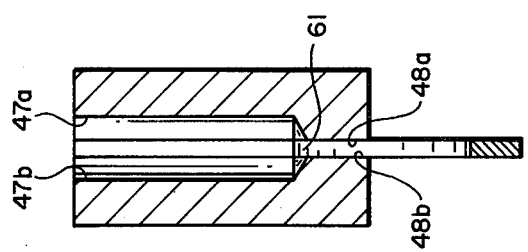
FIG_3
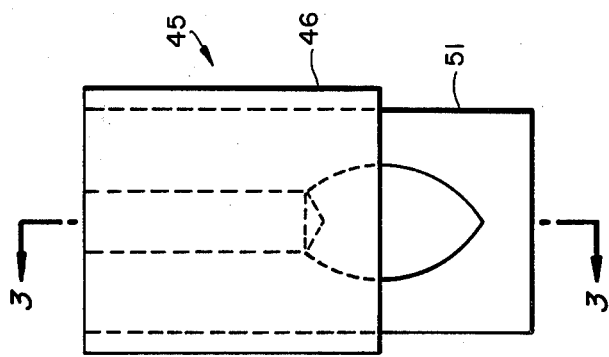
FIG_2
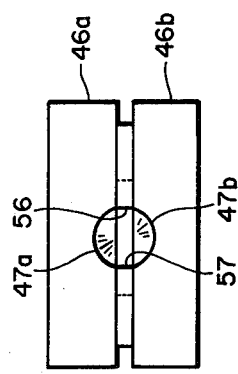
FIG_4

LIGHT SCATTERING PHOTOMETER AND SAMPLE HANDLING SYSTEM THEREFOR

BACKGROUND OF THE INVENTION

1. Field of the Invention

This invention relates to laser light scattering photometers used to measure the size of particles dispersed in liquids and, more particularly, to a particle handling technique wherein the particles are contained in a thin flat unsupported curtain of the liquid which contains the scattering volume.

2. Description of the Prior Art

When a beam of radiant energy (light) is incident upon a particle, a portion of this energy will be scattered. The intensity of this scattered radiant energy depends upon the wavelength of the incident radiant energy, upon the difference in refractive index of the particle with respect to the medium in which it is suspended, upon the size and shape of the particle, and upon the angle at which the scattered energy is observed.

Detailed theory has been developed to describe the properties of the scattered light as a function of particle size and shape and also the inverse problem of determining the properties of the particle from a knowledge of the scattered light. For a particle having a diameter between about 0.1 and 10 times the wavelength of the incident light, the theoretical description of the scattered light is usually referred to as Mie scattering. This scattering theory is well known and is, for example, described in the book entitled *The Scattering of Light*, by Milton Kerker, Academic Press, New York, 1969.

Extensive experimental difficulties, especially for polydisperse systems, are presented when one wishes to take full advantage of the rigorous Mie theory. For an adequate description of size distribution in a polydisperse system, the particles must be individually measured. To obtain size information from scattered light intensity one must know something about the refractive index of the sample and either measure intensity at several angles or at a single very small angle.

At very small angles, where scattering is in the forward lobe, the measurements are greatly facilitated and accuracy is improved. Unfortunately, the minimum scattering angle of most commercial light scattering photometers is between 20° and 30°. In custom instrument the scattering angle has been reduced. However, this has been limited to between 10° and 15° because background signals increase rapidly with a decrease in scattering angle, and the amount of light scattered from smaller particles decreases as the sixth power of particle diameter.

One of the most recent developments in this rapidly evolving field is the measurement of light scattered at small angles using a laser as the source of illuminating radiant energy. The laser provides a narrow beam of intense radiant energy which is both monochromatic and coherent in nature. The intensity of the radiant energy contained in the beam enables greater sensitivities than photometer instruments employing other energy sources.

A low angle laser light scattering photometer is described in an article entitled "Low-Angle Laser Light Scattering" by Wilbur Kaye, Analytical Chemistry, Volume 45, No. 2, pages 221A-225A (February 1973) and in an article entitled "Low-Angle Laser Light Scattering—Absolute Calibration" by W. I. Kaye and A. J. Havlik, Applied Optics, Volume 12, No. 3, pages 541-550 (March 1973). Use of this photometer to measure particle size is described in an article entitled "Low-Angle Laser Light Scattering—Particle Measurement," by Wilbur Kaye, Journal of Colloid and Interface Science, Volume 44, No. 2, pages 384-386 (August 1973). These articles describe a low-angle laser light scattering photometer including a helium-neon laser operating in the $TEM_{00}$ mode, the rays from which are focused by a lens onto a particle sample volume. Certain of the rays scattered from the sample volume through an angle $\theta$, defined by an annulus, are focused by a relay lens onto a field stop. Rays passing through the field stop are focused by an objective lens onto the end-window of a detector. The output of the detector is proportional to the total radiant power, $P_\theta$, falling thereon.

The primary laser beam, attenuated by suitable attenuators, is transmitted through the sample stream in the direction of the incident beam, and is focused by the relay lens through the field stop. These rays, having a radiant powder $P_0$, are focused by an objective lens onto the end-window of the photomultiplier detector. The ratio $P_\theta/P_0$ is directly proportional to the theoretical Mie function, $i_\theta$, for the particle. The Mie function $i_\theta$ in turn is a function of the effective diameter and shape of the particle, its refractive index relative to the dispersant and the wavelength of light.

The particle sample stream described in the beforementioned article includes two thick silica windows and a polytetrafluorethylene, "Teflon," spacer. The sample stream including the particles was sheathed with an 80 times larger stream of carefully filtered liquid flowing at right angles to the laser beam. These two streams were introduced into the Teflon spacer using dual concentric hypodermic needles.

The surfaces of the silica windows were highly polished to reduce scattering. However, a certain amount of scattering will always exist even when the windows are scrupulously cleaned. This background scattering from the windows can mask the light scattered from small particles in the sample stream. In addition, the outer sheath must be very pure and completely particle free or it will contribute noise signals.

The photometer described in the before-mentioned articles is sufficiently sensitive to respond to single particles as small as 0.08 um in diameter. This corresponded to a ratio $P_\theta/P_O$ approximately equal to $10^{-10}$ at a scattering angle $\theta$ of 3.5°. To get liquids, especially water, sufficiently pure and particle free can be very difficult. For example, the article entitled "Liquid-Phase Particulate Contaminants in Water" by Wilbur Kay, *Journal of Colloid and Interface Science*, Volume 46, No. 3, March 1974, pages 543-544 describes the range of contaminants which have been encountered inpure water. Of course any contaminants in the outer sheath will result in an error in the measurement of the particle.

Another problem encountered with a sample cell is air bubbles. Some liquids, notably water, will not wet clean silica surfaces easily. If air does get into the sample cell, it forms a bubble on the silica window. This bubble acts like a lens scattering the incident light and rendering meaningful measurements impossible.

One technique for eliminating the scattering from the silica windows and outer sheath has been to stream the sample solution through a small circular orifice across the laser beam. This works quite well for aerosols where the air stream carrying the particles has essentially no focusing power. However, a thin steam of liquid forms a cylindrical lens. This lens has two detrimental effects. One, the incident beam gets spread out into an eliptical line so that part of the incident light gets detected with the scattered light, and, two, the lens distorts the pattern of the scattered light sufficiently so that absolute calibration to the Mie theory is very difficult.

SUMMARY AND OBJECTS OF THE INVENTION

It is a general object of the present invention to provide an improved light scattering photometer and method.

It is another object of the present invention to provide an improved sample handling technique wherein the particle solution itself is formed into a thin unsupported sample curtain for a low-angle laser light scattering photometer.

It is another object of the present invention to provide a sample handling system in which background scatter is reduced substantially.

It is another object of the present invention to provide an easily regulated dilution system.

It is another object of the present invention to provide a scatering photometer having a field stop consisting of a narrow slot. The narrow dimension of the slot ensures that the detector views only scattered light from particles which pass through the center of the incident beam. The long dimension of the slot, which is in the direction of particle flow, allows a longer time duration pulse of scattered light from the particle which eases the requirementsof the associated measuring circuits.

The foregoing and other objects of the invention are provided by a laser scatter photometer in which the sample particle solution is presented to the laser beam in the form of an unsupported curtain. The photometer may include a field stop consisting of a narrow slot permitting longer viewing of the particle flowing past the beam.

BRIEF DESCRIPTION OF THE DRAWINGS

FIG. 1 is a partially pictorial and partially cross sectional view of the optical elements of a low angle laster light scattering photometer used for measuring radiant power scattered from single particles in accordance with the present invention.

FIG. 2 is a front elevational view of a device for forming a thin flat unsupported curtain of liquid containing the particles to be analyzed.

FIG. 3 is a sectional view taken along the line 3—3 of FIG. 2.

FIG. 4 is a top view of the curtain forming device.

FIG. 5 is an elevational view of the sample support rail used in the curtain forming device.

DESCRIPTION OF THE PREFERRED EMBODIMENTS

Referring now to the drawings and more particularly to FIG. 1, there is shown a light scattering photometer for obtaining particle size distributions. A radiant energy source 11 forms an output beam 12. Preferably, the energy source is a laser. A helium-neon laser operating in the TEM$_{00}$ mode at a wavelength of 633 nm has been found to be suitable. Other more powerful shorter wavelength lasers such as argon and helium-cadmium lasers can be used. The laser output beam 12 is focused by lens 13 so that it has a beam waist in the vicinity of the sample curtain 14 resulting in an intense beam of radiant energy at the sample volume within the fluid curtain 16. The angle of convergence $\beta$ of the incident beam is generally small since the smallest angle $\theta$ relative to the direction of the incident beam at which scattered radiant energy from a particle may be measured without intercepting a portion of the transmitted incident beam is $2\beta$. An aperture 17 serves to block undesired radiant energy.

The curtain 16, which will be described in more detail below, flows downward through the incident beam waist at nominally right angle to the direction of the incident beam. The curtain has a central portion which is substantially flat and planar. The curtain 16 contains the particles to be sized and presents them to the sample volume.

Radiant energy scattered from curtain 16 at an angle $\theta$ is illustrated by rays 18. Rays 19 illustrate radiant energy transmitted through the sample as undeflected incident rays. The rays 19 are reflected as rays 21 by a radiant energy trap 22. The energy scattered both from the fluid and particles within the fluid is intercepted by an annular aperture 23 in mask 24. The mask passes only energy in the incremental angle $\Delta\theta$ at angle $\theta$. Annular aperture 23 is symmetrically located about the axis of the incident beam so that the aperture receives all of the scattered energy from the sample at angle $\theta$ in a conical surface having an apex at curtain 16 and a base formed by aperture 23. The scattered rays 18 are refocused by relay lens 26 into a conical surface having an apex at point 27. The size of point 27 will depend upon the waist of the incident beam at curtain 16.

When it is desired to obtain a measurement of the transmitted incident beam defined by rays 19, trap 22 is removed allowing the rays 19 to pass through a central aperture 28 in mask 24. These transmitted rays then pass through attenuator 29 and relay lens 26 which refocuses them at point 27. Attenuator 29 is a safety attenuator to prevent damage to the detector when trap 22 is removed. Additional calibrated attenuators 31, 32 and 33 may be positioned between source 11 and lens 13 to reduce the intesity of the beam, when measuring the transmitted energy. The attenuators reduce the intensity of the beam to the approximate value of the intensity of the beam when measuring the scattered energy.

A field stop wheel 34 having various size apertures 36 which may be individually selected and symmetrically positioned about point 27 is disposed at the point 27. Aperture 36 allows some percentage of the radiant energy focused onto point 27 to pass through field stop 34. Light trap 22, annular aperture 23, relay lens 26, and field stop 34 combine to admit through aperture 36 only the energy scattered from a small sample volume portion of the sample curtain at angle $\theta$ and to essentially eliminate other undesired radiant energy.

Aperture 36 may be a small circular hole with a diameter not more than about 15% of the size of the incident beam at the curtain. This is to ensure that only particles which pass through the center of the incident beam are detected and that the scattered light will be directly proportional to the Mie function for the particle as described in the before mentioned "Particle Measurements" article. Alternatively and preferably, aperture 36 may be a narrow slot with the narrow dimension not more than about 15% of the size of the incident beam at the curtain and the long dimension, which is parallel to the direction of particle flow, at least as long as the diameter of the incident beam at the curtain.

The radiant energy passing through aperture 36 is refocused by lens 37 onto the photosensitive surface of detector 38 at point 39. Both the scattered rays 18 and the transmitted rays 19, not shown, are converged into conical surfaces having an apex at point 39. Detector 38, which is typically a photomultiplier, detects the scattered or transmitted energy and provides an output signal indicative of the radiant power in each beam. The signal is processed and displayed by a display 41 which may be an oscilloscope or a multichannel analyzer.

Operation of the photometer is now described with reference to FIG. 1. Rays 12 from source 11 are focused by lens 13 onto the sample curtain 16. When a particle traverses the incident beam a small portion of the incident light will be scattered as a short pulse of light. The rays scattered through an angle $\theta$, defined by annulus 23 in mask 24, are focused by relay lens 26 onto aperture 36 of field stop 34. Rays passing through aperture 36 of field stop 34 are focused by lens 37 onto the photomultiplier detector. The electrical output pulse of the detector is proportional to the total radiant power falling on the photocathode and the peak height of the output pulse, $P_\theta$, is proportional to the particle size. At this time, the transmitted energy is blocked by trap 22.

Thereafter, trap 22 is removed and the rays 12 from the laser source 11, attenuated by a selected combination of attenuators 31, 32 and 33 are transmitted through the curtain in the same direction as the incident beam and, after passing through aperture 28 and attenuator 29, are focused onto field stop 34. A larger aperture 36 in field stop 34 is selected allowing all of the attenuated transmitted rays to pass through field stop 34 and be refocused onto point 39 at detector 38. The output of the detector is proportional to the total radiant power $P_O$, falling onto the photocathode. The ratio $P_\theta/P_O$ is directly proportional to the Mie function $i_\theta$ and is utilized to calculate the particle diameter. Normally, many particles, each with their unique $P_\theta$, are measured and the output stored in a multi-channel storage means before measuring $P_O$. In this way, a particle size distribution can be obtained.

In accordance with the present invention, the particles to be measured or analyzed are presented to the focused beam 12 by an unsupported curtain 16. Thus, there are no windows to give rise to reflections, different indices of refraction, and scattering. A suitable device for forming the sample curtain is shown in FIGS. 2 through 5. The device 45 includes a body 46 having first and second portions 46a and 46b. Each of the two portions are machined or otherwise processed to form grooves 47a, 47b having a semicircular configuration. The body may initially be one piece and drilled and then split to form the two body portions 46a, 46b having grooves 47a, 47b, respectively. The faces 48a, 48b of the body portions are polished. A plate 51 is sandwiched between the faces 48a, 48b. The plate includes a cutout 52 defining a pair of arms 53, 54 having spaced parallel surfaces 56, 57. The surfaces 56, 57 are coincident with the adjacent groove walls. The lower end of the cutout flares outwardly in a curved fashion as shown at 58, 59. The widest portion of the curved cutout is at the lower edge of the body portions 46a, 46b. A transition from the circular cross section to rectangular cross section is made at 61. A configuration of the type described resulted in a curtain having uniform thickness substantially equal to the thickness of the plate 51, with flat front and back surfaces whereby there was minimum scatter from the surfaces. It is apparent that other types of curtain forming devices may be employed.

Free falling streams and ribbon shaped curtains have been used for other purposes. U.S. Pat. Nos. 3,691,391, 3,702,403 and 2,535,181 teach a freely flowing sheet of liquid. The patents disclose the use of the flowing sheet to study the physical properties of the liquid such as transmittance, concentration, and turbidity by passing a light directly through the liquid to a detector. U.S. Pat. No. 3,766,489 teaches a free flowing ribbon of laser dye solution placed at Brewster's angle in a dye laser optical cavity. A viscous solvent such as ethylene glycol is employed to promote a smooth-surface flow. Curtain or ribbon forming systems of the type described in these patents may be used in the present invention.

The sample may be injected into the flow system in various ways. As for example it may be mixed in a liquid container in a vessel from which the liquid is applied to the curtain forming device. The preferred system is shown in FIG. 1. It is especially convenient to have a system in which the carrier fluid can be filtered with fairly standard filtering techniques to render the carrier fluid particle free. Reservoir 66 contains the particle free liquid in which the particles to be measured will be injected. Pump 67 draws from this reservoir and forces the fluid through filter 68 to regulator 69. The regulator allows a small portion of this fluid to continue through conduit 71 to curtain forming device 45. The excess fluid is returned via conduit 72 to the reservoir 66. The typical flow rate in conduit 71 is about 60–80 ml/min. A solution of the particles to be measured are injected into conduit 71 at point 75 usually with the aid of a syringe 73 and syringe pump 74. The rate of sample injection can be varied to provide for automatic dilution so that only one particle crosses the incident beam at any instant of time. If the sample is injected in a thin stream, it will flow past the beam in such a manner that all particles are counted to give a total particle count.

The experimental convenience which the flow system of FIG. 1 provides is that (1) the particle free fluid in which the particles will be injected can be monitored for particle content prior to sample injection, (2) by drawing a portion of this fluid into the sample syringe 74 and then injecting it into the fluid stream it can be used to check the cleanliness of the syringe and can also be used as a source for particle dilution of the sample. In addition, there are no windows or confinement sheath.

As mentioned above, the preferred configuration of aperture 36 in field stop 34, when measuring $P_\theta$, is a thin rectangular slot. The reason for this can now be made clear. The particle velocity in the curtain is on the order of 400 cm/sec. and the incident laser beam diameter at curtain 16 is on the order of 80 $\mu$m at the $1/e^2$ points. Therefore a circular aperture 36 must not be larger than 15 $\mu$m for accurate particle sizing, and the scattered light pulse will have a time duration of less than 4 usec. By making aperture 36 a rectangular slot with the long dimension in the direction of particle flow the scattered light pulse is now increased in duration to the time it takes the particle to traverse the entire incident laser beam and its pulse shape will be Gaussian. The increased pulse duration and prior knowledge of pulse shape allow for detection of smaller particles.

It can therefore be seen that in accordance with the present invention, there is provided an improved sample handling system for low angle laser light scattering photometers which solves the problems encountered in the prior art and permits measurement of smaller particles. Sample curtain 16 is completely compatible with a laser photometer having a small beam and a small scattering volume. Sample curtain 16 results in the reduction of background scattering at small angles and reduces the usable scattering angle. This reduction of scattering angle means that the range of particle sizes is increased. In addition, it is apparent that the sample handling system of the present invention can be used in conjunction with photometers for simultaneous multiple measurement techniques such as disclosed in U.S. Pat. No. 3,850,525.

What is claimed is:

1. A light scattering photometer for measuring radiant power scattered by particles dispersed in a liquid comprising means forming a thin, flat curtain of said liquid having substantially parallel spaced unsupported surfaces, means for radiating a small sample volume of the liquid curtain with a beam of radiant power directed substantially perpendicularly through the curtain from one surface to the other and means for detecting the radiant power scattered by particles in said sample volume.

2. A system for measuring the size of particles dispersed in a liquid comprising means forming a thin, flat liquid curtain containing said particles and having at least one portion with substantially parallel spaced unsupported surfaces, means forming and impinging a beam of radiation upon one surface of said curtain at said one portion to radiate a predetermined volume, and means associated with the other surface for sensing only radiation scattered by the particles flowing through the beam at said volume.

3. A system as in claim 2 including means for injecting the particles to be measured into said liquid prior to formation of said curtain.

4. A system as in claim 2 including a liquid reservoir for supplying liquid to said curtain forming means and means are provided for injecting particles into the liquid leaving said reservoir prior to applying said liquid to said means for forming said curtain.

5. A system as in claim 4 including filter means disposed at the outlet of said reservoir for filtering the liquid.

6. A laser photometer including means forming a curtain of liquid sample having substantially parallel spaced unsupported surfaces, means for focusing a beam of radiant energy at a sample volume in the liquid curtain in a direction substantially perpendicular to the surfaces, means for receiving a cone of radiation issuing from the sample volume is an incremental angle $\Delta\theta$ at an angle $\theta$, means for focusing the cone of radiation at a field stop aperture and a detector for receiving the radiation passing through the aperture.

7. A laser photometer as in claim 6 in which said aperture is elongated in the direction of liquid flow so that the radiation is scattered during the time the particle traverses the beam impinging upon the detector.

8. A light scattering photometer as in claim 6 including means for permitting transmitted radiation to pass through said aperture to said detector.

9. A system as in claim 2 including means for injecting the particles to be measured into said liquid curtain in a thin stream so that all the sample particles pass through the said beam of radiation so that total particle count is obtained.

10. A system as in claim 6 including means for injecting the particles to be measured into said liquid curtain in a thin stream so that all the sample particles pass through the said beam of radiation so that total particle count is obtained.

* * * * *